United States Patent
Graumann et al.

(10) Patent No.: US 8,199,876 B2
(45) Date of Patent: Jun. 12, 2012

(54) IMAGING SYSTEM AND METHOD FOR PREPARING X-RAY IMAGES AND OPTICAL IMAGES

(75) Inventors: Rainer Graumann, Höchstadt (DE); Nassir Navab, München (DE)

(73) Assignee: Siemens Aktiengesellschaft, Munich (DE)

( * ) Notice: Subject to any disclaimer, the term of this patent is extended or adjusted under 35 U.S.C. 154(b) by 824 days.

(21) Appl. No.: 12/159,490

(22) PCT Filed: Nov. 17, 2006

(86) PCT No.: PCT/EP2006/068608
§ 371 (c)(1), (2), (4) Date: Nov. 14, 2008

(87) PCT Pub. No.: WO2007/073988
PCT Pub. Date: Jul. 5, 2007

(65) Prior Publication Data
US 2009/0141958 A1   Jun. 4, 2009

(30) Foreign Application Priority Data
Dec. 27, 2005 (DE) .......... 10 2005 062 582

(51) Int. Cl.
*G01N 23/04* (2006.01)
*G06T 7/00* (2006.01)

(52) U.S. Cl. ......... 378/63; 382/132
(58) Field of Classification Search .......... 378/63, 378/198, 206, 98.12; 382/128, 130–132
See application file for complete search history.

(56) References Cited

U.S. PATENT DOCUMENTS

| | | | |
|---|---|---|---|
| 5,539,798 A | 7/1996 | Asahina et al. | |
| 5,923,727 A * | 7/1999 | Navab | 378/207 |
| 6,227,704 B1 | 5/2001 | Bani-Hashemi et al. | |
| 6,229,873 B1 | 5/2001 | Bani-Hashemi et al. | |
| 6,447,163 B1 | 9/2002 | Bani-Hashemi et al. | |
| 6,473,489 B2 | 10/2002 | Bani-Hashemi et al. | |
| 6,895,268 B1 | 5/2005 | Rahn et al. | |
| 2004/0258210 A1 * | 12/2004 | Ritter | 378/198 |

FOREIGN PATENT DOCUMENTS
DE   199 51 503 B4   1/2004

OTHER PUBLICATIONS

Interventions Under Video-Augmented X-Ray guidance: Application to Needle Placement, Mitschke et al., MICCAI 2000, 3rd International Conference Proceedings (Lecture Notes in Computer Science), vol. 1935, pp. 858-868.

* cited by examiner

*Primary Examiner* — Irakli Kiknadze
(74) *Attorney, Agent, or Firm* — Schiff Hardin LLP

(57) ABSTRACT

In an imaging system and method for preparing x-ray images and optical images, at least two x-ray images of an examination subject are acquired by emitting x-rays from at least two different x-ray image acquisition points in space. At least two optical exposures are acquired from the examination subject at respective optical exposure origination points that respectively optically correspond to the x-ray image acquisition points. The optical exposures and the x-ray images are superimposed so that each optical image is superimposed with the x-ray image that originated from an x-ray image origination point corresponding to the optical exposure origination point of that optical exposure.

16 Claims, 5 Drawing Sheets

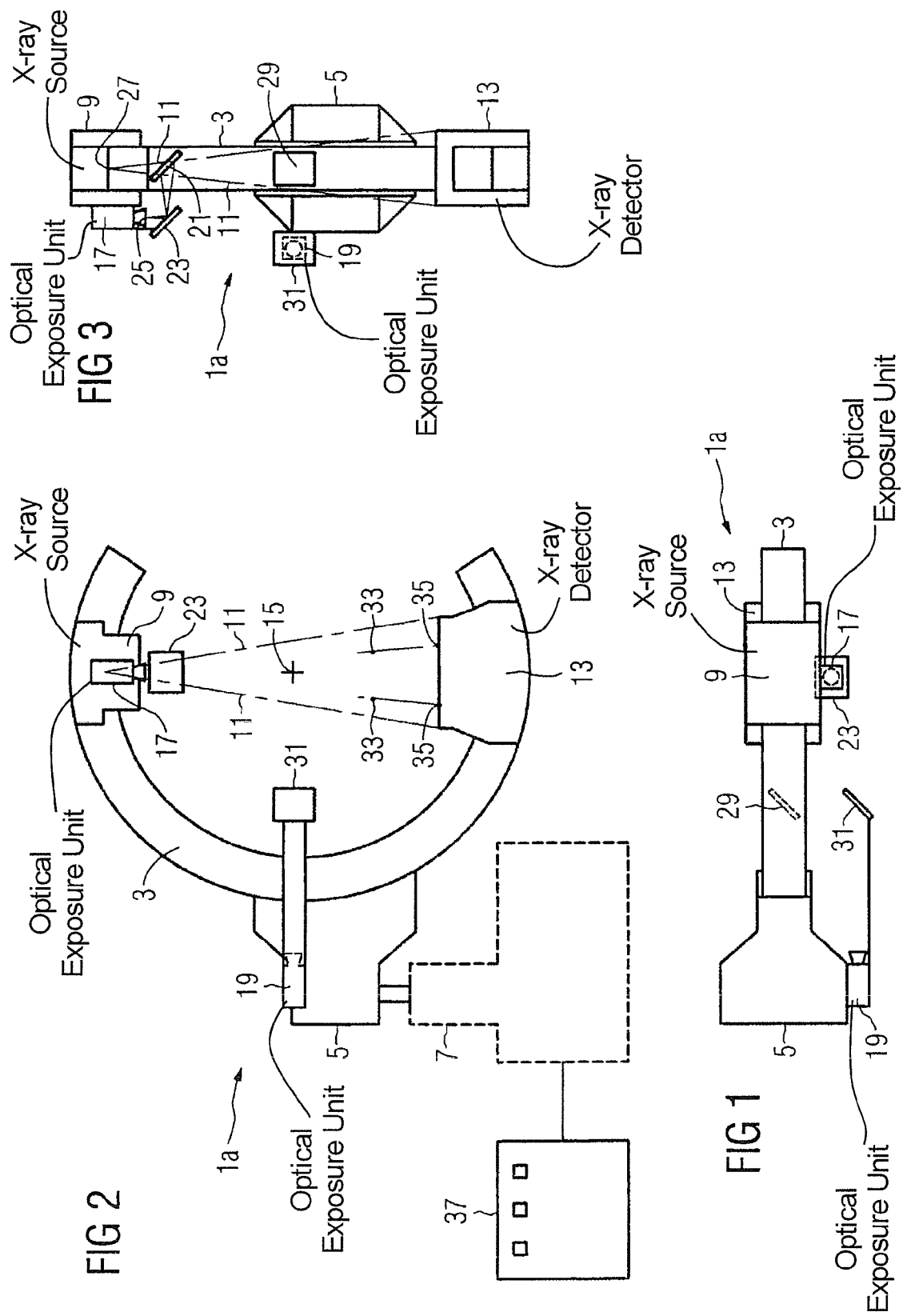

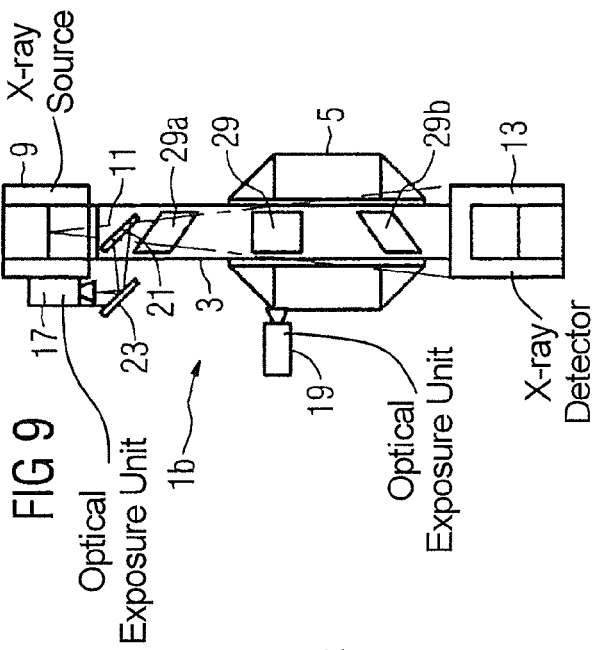
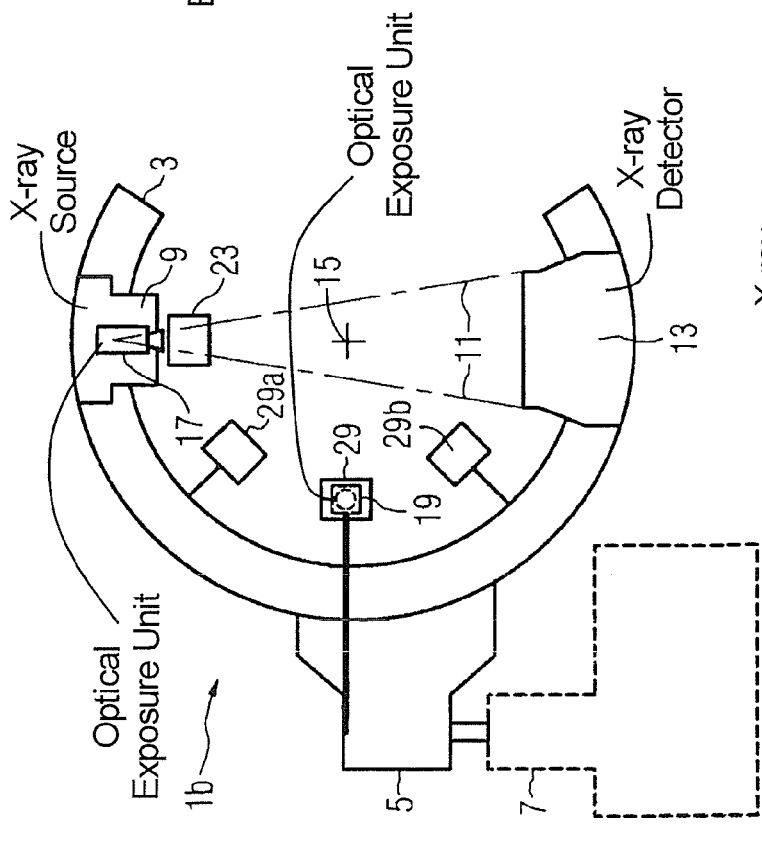
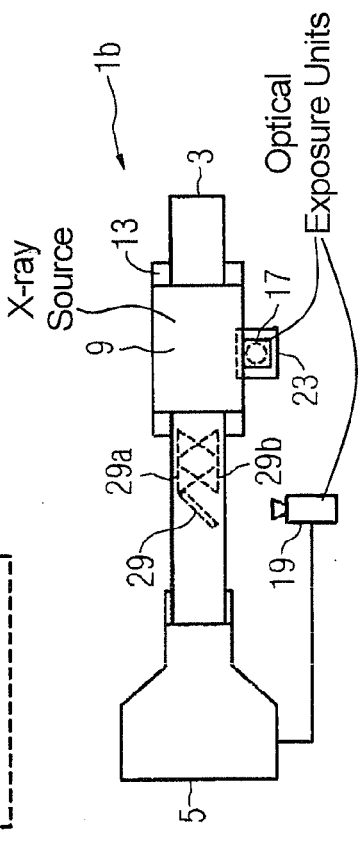

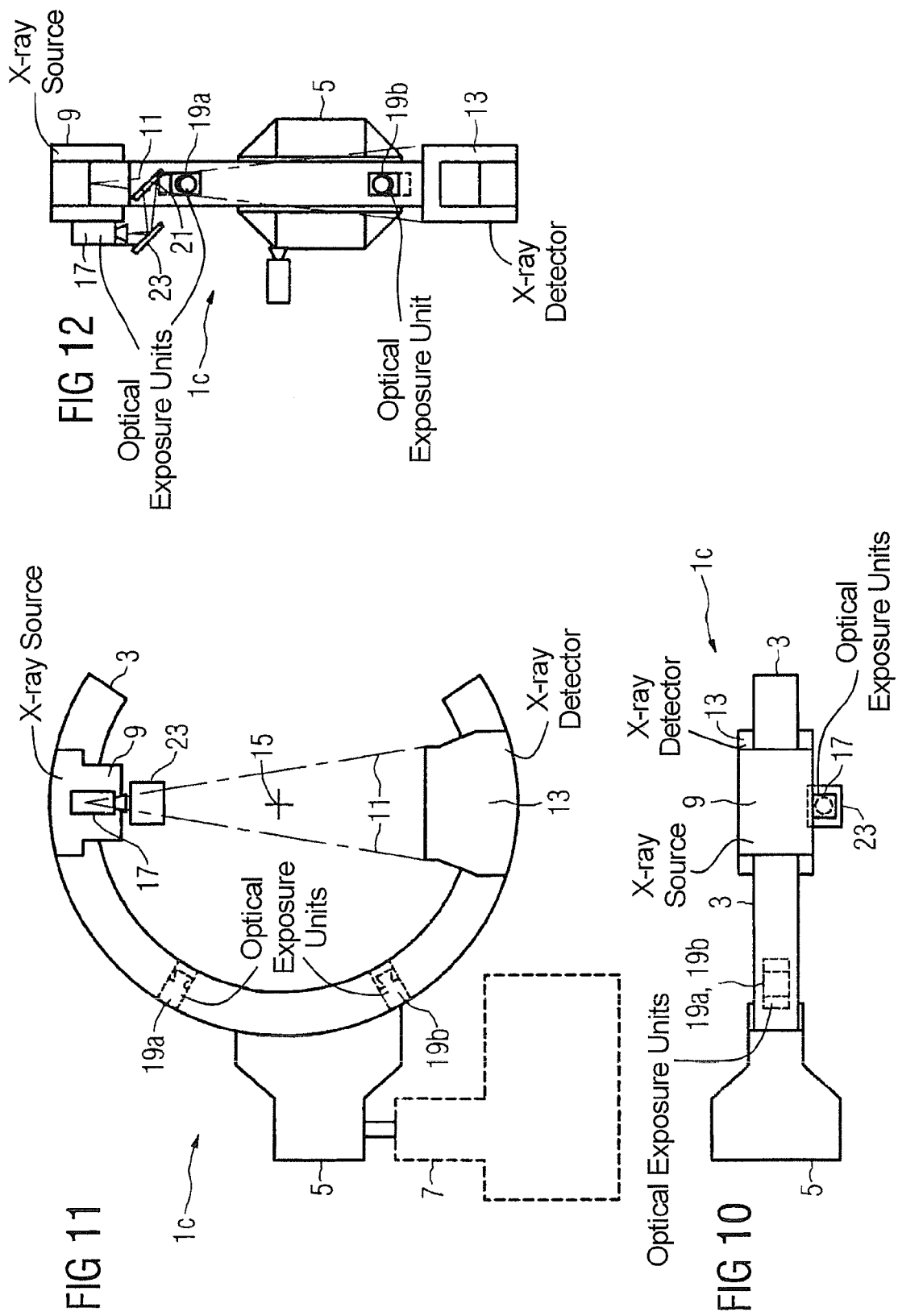

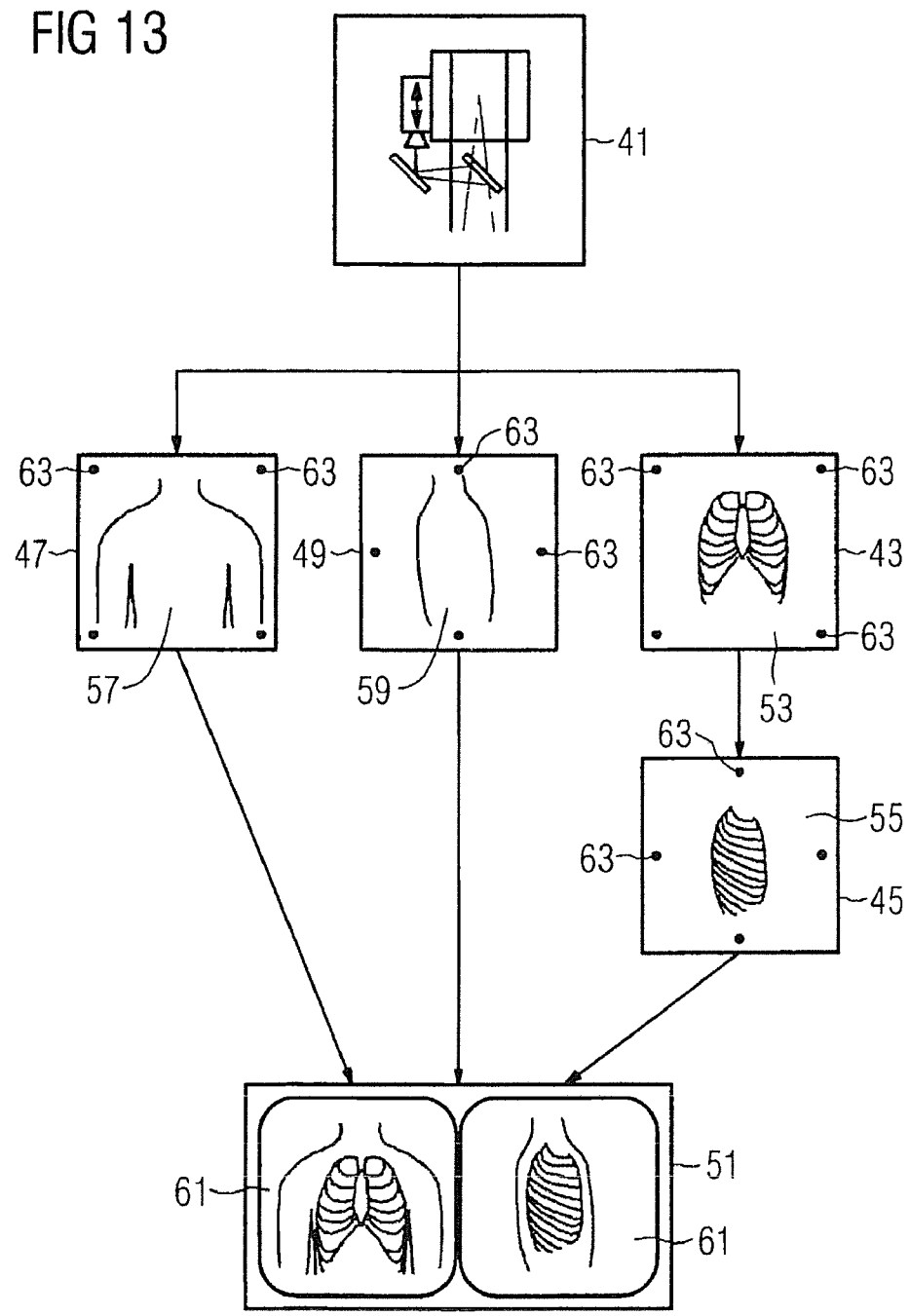

IMAGING SYSTEM AND METHOD FOR PREPARING X-RAY IMAGES AND OPTICAL IMAGES

BACKGROUND OF THE INVENTION

1. Field of the Invention

The present invention concerns an imaging system and a method for producing x-ray images and optical images as they are in particular used in the production of medical images.

2. Description of the Prior Art

Imaging systems in which two-dimensional projection images of a subject to be examined are produced with x-rays have been successfully used in a known manner in medical imaging for decades. In spite of modern methods of three-dimensional imaging, such imaging systems are frequently used due to their simple and fast handling and their cost-effective operation. Examples are C-arm apparatuses as they are used in an operating room to produce intra-operative images.

In such a C-arm apparatus an x-ray source and an x-ray detector are arranged at opposite ends of a C-shaped arc. The C-arm is rotated around the patient in the production of an exposure so that a two-dimensional projection image can be produced. Countering the advantage of the simple and cost-effective availability of such images is the disadvantage that such images demand of the user a high degree of abstraction capability, since the user only sees a two-dimensional projection of the organs to be examined. For example, given complicated fractures only a user with good spatial imagination can conclude the actual prevailing relationships from two-dimensional projection images, such that misjudgments are not a rarity.

Additionally, in operative procedures (in which it is important to assess the position of surgical instruments) it is a prevalent practice to produce a number of x-ray images in order to detect the movement of the surgical instrument in the operative field. This is often associated with a high radiation exposure for the patient.

Apparatuses as they are disclosed in U.S. Pat. No. 6,473,489 B2, and U.S. Pat. Nos. 6,447,163 B1, and 6,229,873 B1 and U.S. Pat. No. 6,227,704 B1 provide an assistance for the user. In addition to the two-dimensional projection x-ray image, an optical image of the subject to be examined is produced in such apparatuses. Both images coincide in their viewing angle, meaning that the optical beam path and the beam path of the x-rays correspond with one another so that a reasonable superimposed presentation of both images can be implemented. A user can thereby assess features of the projection x-ray image relative to features of the surface of the subject.

Such apparatuses have proven to be helpful in interventional procedures. For example, given a surgical treatment of a fracture a physician can initially produce an x-ray image of the fracture. This x-ray image is superimposed on the optical image. If the physician moves a surgical instrument, he can for the most part track the movement of the instrument via the optical image (for example via a video sequence). Since the optical image and the x-ray image are shown superimposed, from the optical presentation of the instrument the physician can thus conclude its spatial position in the operative field, such that fewer x-ray images must be produced. New x-ray images must be produced only when the fracture relationships change due to the operation.

However, in spite of the additional optical image the danger of a misjudgment of the actual prevalent relationships also arises here (albeit to a lesser degree), in particular if the orientation of the surgical instrument in the optical image is ambiguous in relation to the x-ray image due to the projection.

A system with which an image of a first subject (for example a patient) can be acquired is known from DE 199 51 502 A1. Furthermore, the position from which the image was produced and the position of a second subject (for example a surgical instrument) can be determined with the system, such that now the second subject can be mixed into the image of the first subject. An exposure of the patient with x-rays can also be reduced via such a system since a movement of the instrument can be tracked via the position determination. However, the use of a position determination system in an operating room is comparably complicated. Moreover, the use of conventional surgical instruments is not possible since these do not interact with the position determination system.

SUMMARY OF THE INVENTION

It is an object of the invention to provide an imaging system and method in which optical presentations and x-ray images of a subject can be combined so that a user is supported in an improved manner in the spatial assessment of the subject and/or an instrument in relation to the subject, with simultaneously lower radiation exposure for the user and for the subject.

The above object is achieved in accordance with the present invention by an imaging system that includes an x-ray imaging apparatus that produces two x-ray images of an examination subject respectively using x-rays originating from two different x-ray image origination points in space relative to the examination subject, an optical exposure system that acquires at least two optical exposures of the examination subject from at least two optical exposure originating points in space that respectively optically correspond to the at least two x-ray image origination points, and a superimposition unit that superimposes the respective optical exposures with the respective x-ray images having x-ray image origination points that correspond to the optical exposure origination points.

Using such an imaging system it is possible to produce x-ray images of the subject to be examined from at least two different directions. In addition to the two x-ray images, it is furthermore possible to acquire at least two optical exposures of the subject, and in fact respectively from points that optically correspond to the points from which x-rays have been directed onto the subject. X-ray images and optical exposures are thereby acquired of which one x-ray image and one optical exposure respectively correspond to one another in terms of their perspective.

As used herein an optical exposure means a presentation in which the representation of the subject ensues with optical means, thus (for example) by producing an optical image or—in a preferred embodiment—a video sequence.

The superimposition unit may be an appropriately programmed computer that properly superimposes the x-ray images and the optical exposures depending on the respective origination points.

For example, marker points can be provided for this purpose in the acquisition that appear both in the x-ray image and in the optical exposure in a region (for example the image border) that is unimportant for the subject depiction. An adaptation of the x-ray images and the optical exposures for a superimposed depiction can now ensue in a simple manner. An x-ray image and the associated optical exposure are respectively scaled and positioned using the marker points so that the marker points of the optical exposure and the marker points of the corresponding x-ray image overlap in the superimposed depiction.

An associated optical exposure of the surface of the subject to be examined is additionally shown to a user in an x-ray image via the imaging system according to the invention. Moreover, the imaging system enables such combined image depictions to be produced and presented from at least two different viewing directions so that the user is aided in forming a spatial perception of the subject to be examined. Ambiguities in the interpretation of the spatial relationships in the subject are reduced since depth information is also obtained in addition to the two-dimensional image information via the use of two two-dimensional combined image depictions from different viewing directions.

Such imaging systems according to the invention are very helpful, for example in interventional procedures since the surgeon often only sees the surface from the outside. The surgeon can regain this visual impression in the optical exposure in which the x-ray image is additionally superimposed, such that the surgeon receives a perception of the position of the internal organs (for example of bone fragments given a fracture). Furthermore, such optical exposures are presented to the surgeon from different directions such that he can now significantly better estimate how, for example, the bone fragments are situated in reality or the three-dimensional position of a surgical instrument (for example of a bone nail) relative to the bone fragments. Due to the improved spatial impression of the depiction, fewer x-ray exposures must also be produced since misinterpretations of the x-ray image occur more seldom.

In a preferred embodiment, the at least two optical exposures are two video sequences that are advantageously produced simultaneously.

It is thus possible to track the movement of a medical instrument in the video sequences. In that the corresponding x-ray images are superimposed on the video sequences, the movement of the medical instrument can additionally be tracked in relation to the spatial conditions in the operative field—for example the position of the bone fragments or of a marking nail—without multiple x-ray images having to be produced or the movement of the instrument even having to be tracked under radioscopy.

Only when the spatial conditions of the operative field significantly change due to the procedure—for example, when bone fragments are set or material for osteosynthesis are introduced—are new x-ray images produced in order to thereupon work again with the video sequences that do not incur radiation exposure.

The imaging system preferably has a positioning unit with which the optical system can be positioned such that the points from which the optical exposures are acquired optically correspond to the points from which the x-rays are directed at the subject. With such a positioning unit the optical system can be positioned after the initial application or readjusted in the course of the operation so that the x-ray representations and the optical displays can be produced from the same perspective.

Such a positioning unit is disclosed in U.S. Pat. Nos. 6,447, 163 B1 and 6,227,704 B1.

For example, the positioning unit can include markers that are located in the beam path of the x-rays but are applied outside of the plane of an x-ray detector. Additional projection markers in the plane of the x-ray detector are additionally located in the x-ray projection direction of the markers. Optical exposures of these markers are now acquired. As explained in U.S. Pat. No. 6,447,163 B1, the markers and the projection markers now coincide in an optical exposure only when the beam path of the x-rays and the beam path of the light correspond to one another in the production of the optical exposures. The positioning of the optical system can thus be monitored in a simple manner and be readjusted as needed.

Another possible embodiment of the positioning means comprises a laser beam that is directed from the center of a detector for x-rays onto the point from which x-rays are directed onto the detector. As disclosed in U.S. Pat. No. 6,227, 704 B1, the laser beam is also reflected from the optical means and only strikes the center of the detector plane again when the point from which the optical depicters are acquired and the point from the which the x-rays are directed onto the subject optically correspond with one another.

The imaging system that produces at least two x-ray images preferably has only one mobile x-ray source and only one mobile detector unit for x-ray radiation in order to be able to form the imaging system in a more cost-effective and compact manner.

The imaging system that produces at least two x-ray images is advantageously a C-arm x-ray apparatus. In such a C-arm x-ray apparatus an x-ray source and a detector for x-ray radiation are arranged at the opposite ends of a C-arm. The at least two x-ray images can be produced in a simple manner from different directions by rotating the C-arm.

In one embodiment of the imaging system fashioned as a C-arm x-ray apparatus, the optical system can include at least two image acquisition units (for example video cameras) that are arranged in different position on the C-arm. Via rotation of the C-arm the x-ray source and the image acquisition units are respectively positioned such that the points from which the x-rays are directed at the subject and the points from which the image acquisition units distributed along the C-arm acquire the optical exposures of the subject optically correspond with one another.

In a further embodiment of the imaging system fashioned as a C-arm x-ray apparatus, the optical system has at least two image acquisition units, of which one image acquisition unit is arranged in the region of the x-ray source and the other image acquisition unit is arranged in the region of a support unit for a C-arm.

In a preferred embodiment, at least two mirrors via which optical exposures of the subject can be produced by the at least two image acquisition units are arranged along the C-arm. The mirrors are arranged such that the points from which the optical exposures are acquired optically correspond to the points from which the x-rays are directed at the subject. If the mirrors are x-ray-permeable, they can also be arranged in the beam path of the x-rays.

In an embodiment, the image acquisition units are fashioned as video cameras with which video sequences can be produced as optical exposures of the subject. The video sequences of the subject are thereby produced and shown to the user in real time. The associated x-ray images are superimposed in the presentation of the video sequences. For example, the user can be informed about the movement of a medical instrument via the observation of the video sequences produced in real time.

The above object also is achieved in accordance with the present invention by an imaging method that includes the step of acquiring at least two x-ray images of an examination subject from at least two different x-ray image origination points in space, from which x-rays are directed onto the examination subject, optically acquiring at least two optical exposures of the subject from at least two optical exposure origination points that respectively optically correspond to the at least two x-ray image origination points, and superimposing each optical exposure with the x-ray image having an x-ray image origination point that corresponds with the optical exposure origination point thereof.

The at least two optical exposures are advantageously two video sequences of the subject. As depicted above, the movement of a medical instrument can hereby be tracked in relation to the spatial conditions of the operative field, wherein a patient or a physician is exposed only to a slight x-ray radiation.

In a preferred embodiment, the optical system acquires optical exposures that are positioned such that the at least two points from which the at least two optical exposures are acquired optically correspond to the at least two points from which the x-rays are directed at the subject. This preparation procedure is applied before a first execution of the method in order to achieve a correlation of the optical exposure with the x-ray images. It can also be implemented to recalibrate the system in running operation. The implementation of this preparation procedure is described in U.S. Pat. No. 6,447,163 B1 and U.S. Pat. No. 6,227,704 B1.

In an embodiment, a C-arm x-ray apparatus is used as the x-ray imaging apparatus and carries the optical exposure system that acquires the at least two optical exposures. In this embodiment, one of the at least two x-ray images is acquired with the C-arm of the C-arm apparatus at a first position, and the C-arm is moved to another C-arm position, at which another of the at least two x-ray images is acquired. The at least two optical exposures also required with the C-arm at the aforementioned positions at which the at least two x-ray images were respectively acquired.

The at least two optical exposures of the subject (in particular the video sequences) are preferably produced simultaneously.

BRIEF DESCRIPTION OF THE DRAWINGS

FIG. 1, FIG. 2, and FIG. 3 respectively show a plan view, a side view and a front view of a C-arm apparatus in which an optical image acquisition unit is arranged at the x-ray source, and an additional optical image acquisition unit is arranged on the stand that supports the C-arm.

FIG. 7, FIG. 8 and FIG. 9 respectively show a plan view, a side view and a front view of a further embodiment of a C-arm apparatus, wherein additional mirrors are arranged along the C-arm.

FIG. 10, FIG. 11 and FIG. 12 respectively show a plan view, a side view and a front view of a C-arm x-ray apparatus in which multiple optical image acquisition units are arranged along the C-arm.

FIG. 13 schematically illustrates basic method steps in an embodiment of a method in accordance with the present invention.

DESCRIPTION OF THE PREFERRED EMBODIMENTS

Figure 6:
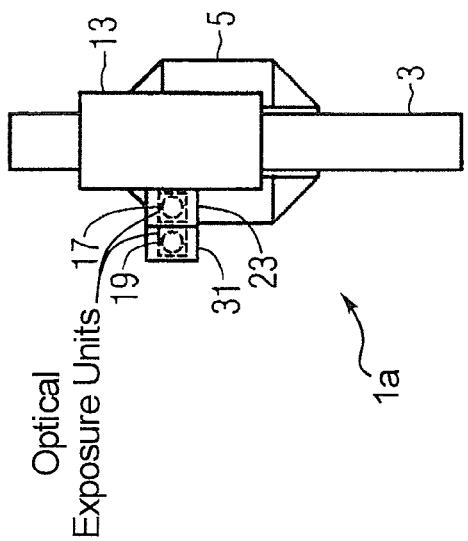
FIG. 4, FIG. 5 and FIG. 6 respectively show a plan view, a side view and a front view of the C-arm x-ray apparatus in FIGS. 1, 2 and 3, with the C-arm located in a different position.

FIG. 1 through FIG. 3 respectively show a plan view, a side view and a front 1 view of a C-arm x-ray apparatus that is additionally fashioned with an optical system to acquire at least two optical exposures.

The C-arm x-ray apparatus 1a has a C-arm 3 that is mounted such that it can move on a support part 5. The support part 5 is part of a stand 7 that is indicated only in outline in FIG. 2 for clarity. An x-ray source 9 for x-rays 11 and a detector 13 for x-rays 11 are located at the opposite ends of the C-arm 3. A subject to be examined, for example, a patient (not shown) is located in the center 15 of the C-arm 3. Since the C-arm 3 is mounted such that it can move in the support part 5, x-ray images of the subject to be examined can be produced from different directions.

The C-arm x-ray apparatus 1a is equipped with optical image acquisition units 17, 19 with which optical exposures of the subject to be examined are produced. Such image acquisition units 17, 19 can be video cameras, for example. In this case the optical exposures are video sequences of the subject to be examined.

An image acquisition unit 17 is arranged on the x-ray source 9. Optical exposures of the subject to be examined can be produced therewith using two mirrors 21, 23. The mirrors 21, 23 are arranged such that the point 25 from which the image acquisition unit 17 acquires the optical exposure corresponds to the point 27 from which the x-rays 11 are directed at the subject. For this the mirror 21 arranged in the x-ray path is fashioned such that it is transparent to x-rays 11.

A further image acquisition unit 19 is arranged on the support part of the stand. Here two additional mirrors 29, 30 ensure that the image acquisition unit 19 acquires an optical exposure of the subject to be examined from a middle, central viewing direction. This direction corresponds to the direction of the x-rays as they are radiated from the x-ray source 9 given a C-arm 3 rotated by 90°, as is described further below.

A portion of the mirrors 23, 31 is thereby fastened on the image acquisition units 17, 19 via mountings. For clarity the mountings are indicated only with lines. However, the mirrors 23, 31 can also be fastened on other components of the C-arm x-ray apparatus 1a if this appears advantageous. For example, the mirrors 21, 23 (that are centrally arranged relative to the C-arm 3) can be fastened on the C-arm 3 itself via mountings (not shown here).

Furthermore, a positioning unit for positioning the image acquisition units 17, 19, as disclosed in U.S. Pat. No. 6,447,163 B1 is shown in FIG. 2. Such a positioning unit includes markers 35 that lie in the detector plane and projection markers 33 that are located outside of the detector plane. Their position is thereby matched to one another such that the projection markers 33 and the markers 35 lie in the beam path of the x-rays in the projection direction. The markers 35 and projection markers 33 thus coincide in an acquired x-ray image.

Given an optical exposure of the markers 35 and the projection markers 22 that is acquired with the image acquisition unit 17 arranged at the x-ray source, markers 35 and projection markers 33 coincide only when the point 25 from which the image acquisition unit 17 produces the optical exposure optically corresponds to the point 27 from which the x-rays are directed at the markers 35 and projection markers 33.

With this method the position of the image acquisition unit 17 is adjusted until it acquires optical exposures from a point 25 that optically corresponds with the point 27 from which the x-rays 11 are emitted to the subject. For clarity the markers 35 and projection markers 33 have not been shown in FIG. 1 and FIG. 3.

The positioning of the image acquisition unit 19 arranged on the stand 7 ensues in an analogous manner on a C-arm 3 rotated 90°.

The positioning unit for positioning the image acquisition units 17, 19 is formed in this embodiment by using markers 35 and projection markers 33.

However, other means can also be used (for example laser beams) that are directed from the detector plane to the image acquisition unit 17 and are reflected by this, as disclosed in U.S. Pat. No. 6,227,704 B1.

A computer 37 with which the optical exposures acquired by the image acquisition units can be superimposed with the x-ray images is likewise drawn in FIG. 2. The presentation of the superimposed x-ray images and optical exposures can ensue via a monitor, for example.

In the position of the C-arm 3 shown here, an x-ray image of the subject to be examined is produced with a beam path from top to bottom. Of the two optical 2 exposures of the subject that are produced from different directions, the produced x-ray image is superimposed with that optical exposure that was acquired by the image acquisition unit 17 arranged at the x-ray source 9 in order to obtain an exposure that shows the external surface of the subject to be examined and shows the associated x-ray image from the same perspective.

In order to acquire an x-ray image that is acquired from the same perspective with which an optical exposure of the subject is acquired by the image acquisition unit 19 fastened on the stand 7, the C-arm 3 is brought into a position perpendicular to the original position.

Figure 5:
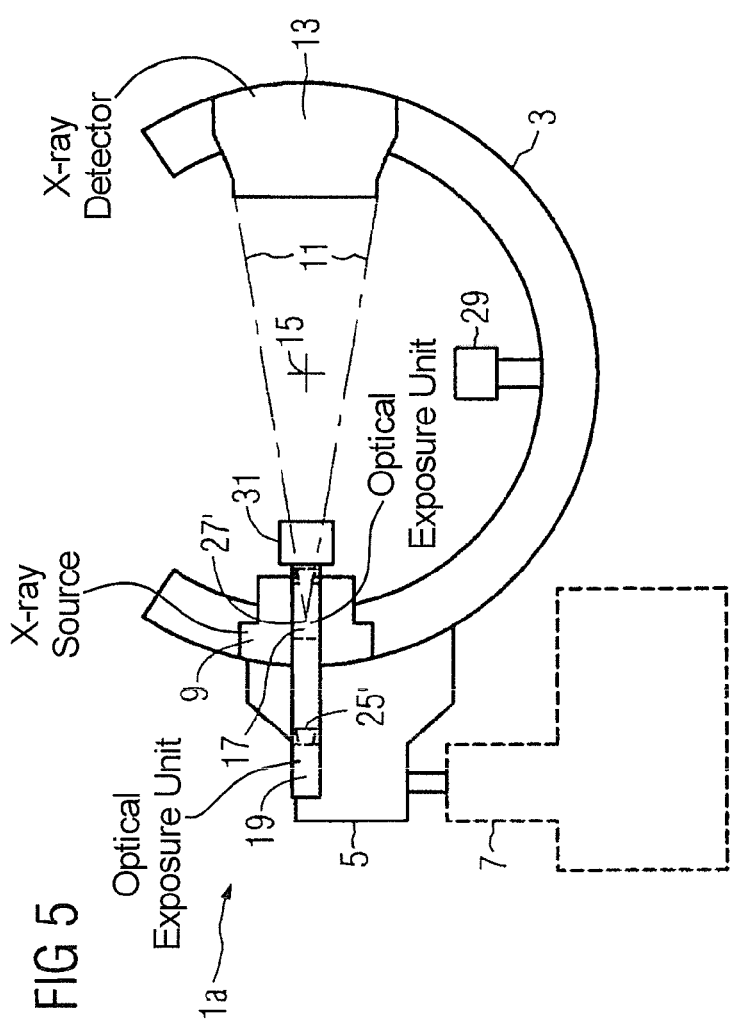
Figure 4:
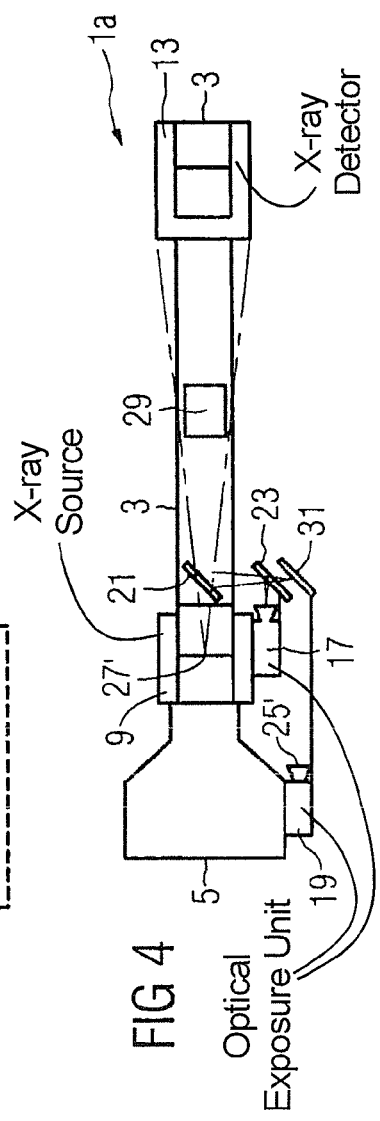

This position of the C-arm 3 is respectively shown in a plan view and a front view in FIG. 4 through FIG. 6. In this position of the C-arm 3, the x-rays 11 are directed from a point 27' to the subject to be examined, which point 27' optically corresponds with the point 25' from which an optical exposure of the subject is produced with the image acquisition unit 19 fastened on the stand 5. In this manner two image pairs are acquired that respectively comprise an optical exposure and an x-ray image that were acquired from the same perspective.

If the two image pairs are shown superimposed to a user (for example a physician who conducts an operation), the physician can gain a distinctly better spatial impression of the operative field in a simpler manner. The physician can achieve a good spatial impression with the aid of the two image pairs primarily in operations in which the operative field is not entirely open and therefore cannot be viewed, for example given the surgical treatment of bone fractures. In addition to the two-dimensional information that the user can learn from the two image pairs, the user receives depth information via the other of the two image pairs.

If video sequences of the subject to be examined are acquired via correspondingly designed image acquisition units 17, 19, over which video sequences the two produced x-ray images are then laid, a physician can additionally track the movement of interventional instruments that are used in the operation and can place the position of the instruments in relation to the operative field via the x-ray images. Projection-dependent ambiguities in the interpretation of the spatial position of the instruments that would result given the use of only one image pair are distinctly reduced via the use of at least two image pairs.

In that the movement of the interventional instruments is tracked with the image acquisition units 17, 19, the physician and the patient are exposed to a distinctly lower radiation exposure. New x-ray images must only be produced when the spatial situation in the operative field significantly changes in the course of the procedure (for example when bone fragments are realigned with one another), which new x-ray images are then in turn superimposed with the optical exposures and presented.

The position of the C-arm 3 shown in FIGS. 4 through 6 furthermore entails the advantage that a correct positioning of the two image acquisition units 17, 19 can be checked in a simple manner. If both optical exposures that are acquired in this position by the two image acquisition units 17, 19 do not coincide, the position of one or both image acquisition units 17, 19 must be recalibrated. The mirror 23 that deflects the light to the image acquisition unit 17 that is arranged at the x-ray source 9 is thereby fashioned semi-transparent.

In the C-arm x-ray apparatus 1*a* shown in FIG. 1 through FIG. 6, the mirrors 21, 23, 29, 31 are arranged such that the apparatus is suitable for the production of two optical or, respectively, x-ray images from two directions perpendicular to one another. The viewing directions from which the optical exposures of the subject are produced can be adjusted via a suitable mounting of the mirror 29 that is arranged centrally relative to the C-arm at the angle position of 90°, for example at an angle position of 60°.

Different angles between the two viewing directions can be selected by mounting multiple mirrors 21, 29, 29*a*, 29*b* along the C-arm x-ray apparatus 1*b*, for example at angle positions of 45°, 90° and 135°. Such a C-arm x-ray apparatus 1*b* is shown in FIG. 7 through FIG. 9. In comparison to the C-arm x-ray apparatus 1*a* shown in FIG. 1 through FIG. 6, additional mirrors 29*a*, 29*b* are arranged here at angle positions of 45° to 135°. Not only can image pairs be produced in which the two viewing directions exhibit an angle of 90°; rather, image pairs with viewing direction angles of 45° to 135° can also be produced.

An alternative mounting of the image acquisition unit 19 arranged on the stand is additionally shown in FIG. 7 through FIG. 9.

FIG. 10 through FIG. 12 respectively show a plan view, a side view and a front view of a C-arm x-ray apparatus 1*c* in which multiple image acquisition units 17, 19*a*, 19*b* are arranged along the C-arm 3. In contrast to the C-arm apparatuses 1*a*, 1*b* disclosed above, additional image acquisition units 19*a*, 19*b* are arranged in the C-arm (here at angle positions of 60° and 120°, for example) in addition to the image acquisition unit 17.

The C-arm x-ray apparatus 1*c* shown here has the advantage that more than two image acquisition units 17, 19*a*, 19*b* simultaneously produce optical exposures of the subject to be examined from different perspectives. The associated x-ray images corresponding to the angle positions of the image acquisition units 17, 19*a*, 19*b* are produced in that the x-ray source 9 is moved to the corresponding points via a rotation of the C-arm 3. This apparatus thus possesses the advantage that more than two image pairs of the subject to be examined are produced, which can be helpful in particular in the assessment of complicated geometric relationships.

FIG. 13 schematically shows the method steps of a preferred embodiment of the method.

The method steps shown here can be executed with a C-arm x-ray apparatus 1*a* as shown in FIG. 1 through FIG. 6 in which two different optical exposures 57, 59 and two different x-ray images 53, 55 are produced and superimposed.

However, the method explained here is only explained by way of example with the C-arm x-ray apparatus 1*a*. The number of the corresponding x-ray images and optical exposures is in particular not limited to two image pairs given corresponding design of an acquisition system.

In a pre-method 41 the optical system is initially positioned such that the two points 25, 25' from which the optical exposures 57, 49 are acquired optically correspond to the points 27, 27' from which the x-ray images 53, 55 are produced.

An x-ray image 43 of a patient to be examined is produced in a first method step 43 upon implementation of the actual method. Given production of the x-ray image 43 the C-arm 3 of the C-arm apparatus 1*a* is located in a specific position. An additional x-ray image 45 is produced in a second method step 45, this time from a different direction. In the course of the operation a respective optical exposure 57, 59 of the patient to be examined is produced in a third and fourth method step 47 or, respectively, 49 from the directions corresponding to the x-ray images 53, 55. In a specific embodiment, video sequences of the patient to be examined are acquired as optical exposures 57, 59.

In a fifth method step 51 the respective corresponding x-ray images and optical exposures (or video sequences) 53, 57 or, respectively, 55, 59 are superimposed and presented to a user who receives a distinct, three-dimensional impression of the patient to be examined via the superimposition 61 of the two image pairs that were produced form two different directions. This represents a significant facilitation for a treating physician, in particular in interventional procedures. If video sequences are used as optical exposures, the physician can moreover track the movement of interventional instruments (as described further above) and associate these with the spatial conditions in the operative field via the x-ray images without using an x-ray radioscopy or a multiple production of x-ray images.

The superimposition is typically executed by a correspondingly fashioned computer 37. The x-ray images 53, 55 and optical exposures 57, 59 can be provided with marker points 63 for simpler superimposition.

In summary, the invention is based on the concept of generating these two x-ray images of a subject with x-rays respectively directed at the examination subject from at least two different points in space, and obtaining at least two optical exposures of the examination subject respectively from two different optical exposure origination points that respectively correspond to the at least two different points in space from which the x-ray images were obtained, with the optical exposures and the x-ray images being respectively superimposed dependent on their respective origination points.

Although modifications and changes may be suggested by those skilled in the art, it is the intention of the inventors to embody within the patent warranted heron all changes and modifications as reasonably and properly come within the scope of their contribution to the art.

We claim as our invention:

1. An imaging system comprising:
   an x-ray imaging system comprising a C-arm that is movably mounted at a support unit and a single x-ray source am a single x-ray detector mounted on said C-arm, said x-ray imaging system being configured to acquire at least two x-ray images of an examination subject respectively by irradiating the examination subject with x-rays directed at the subject from at least two different x-ray image origination points in space by movement of said C-arm with said single x-ray source and said single x-ray detector mounted thereon;
   an optical imaging system comprising at least two optical image acquisition units, a first of said optical image acquisition units being mounted for co-movement with said single x-ray source, and a second of said optical image acquisition units being mounted at said support unit, said optical system being configured to acquire at least two optical exposures of the examination subject respectively from at least two optical exposure origination points that respectively optically correspond to said at least two different x-ray image origination points; and
   a superimposition unit that superimposes the optical exposures with the x-ray images by superimposing the respective optical exposure, from among said at least two optical exposures, with the respective x-ray image, from among said at least two x-ray images, that has an x-ray image origination point corresponding to the optical exposure origination point of that optical exposure.

2. An imaging system as claimed in claim 1 wherein said optical system is configured to acquire each of said at least two optical exposures as a video sequence.

3. An imaging system as claimed in claim 1 wherein said optical system is configured to acquire said at least two optical exposures simultaneously.

4. An imaging system comprising:
   a C-arm imaging system comprising a C-arm that is movable to allow said C-arm x-ray imaging system to acquire at least two x-ray images of an examination subject respectively by irradiating the examination subject with x-rays directed at the subject from said at least two x-ray image origination points in space;
   an optical imaging system that acquires at least two optical exposures of the examination subject respectively from at least two optical exposure origination points that respectively optically correspond to said at least two different x-ray image origination points, said optical system comprising at least two optical image acquisition units and, for each of said optical image acquisition units, at least two mirrors, said at least two optical image acquisition units and the at least two mirrors associated therewith being respectively positioned to direct light from the examination subject via the at least two mirrors to the associated optical image acquisition unit to respectively acquire said at least two optical exposures at said optical exposure origination points respectively corresponding to said at least two x-ray image origination points; and
   a superimposition unit that superimposes the optical exposures with the x-ray images by superimposing the respective optical exposure, from among said at least two optical exposures, with the respective x-ray image, from among said at least two x-ray images, that has an x-ray image origination point corresponding to the optical exposure origination point of that optical exposure.

5. An imaging system as claimed in claim 4 wherein said C-arm x-ray imaging system comprises a single movable x-ray source and a single movable x-ray detection unit, both mounted on said C-arm.

6. An imaging system as claimed in claim 5 wherein said at least two optical image acquisition units are respectively mounted at different positions on said C-arm.

7. An imaging system as claimed in claim 5 comprising a support unit on which said C-arm is movably mounted, and wherein said optical system comprises at least two optical image acquisition units, a first of said at least two optical image acquisition units is mounted for co-movement with said x-ray source, and a second of said at least two optical image acquisition units is mounted at said support unit.

8. An imaging system as claimed in claim 4 wherein each of said optical image acquisition units is a video camera.

9. An imaging method comprising the steps of:
   with a C-arm that is movably mounted on a support unit and that has a single x-ray source and a single x-ray detector mounted on the C-arm, acquiring at least two x-ray images of an examination subject respectively by irradiating the examination subject with x-rays directed at the subject from at least two different x-ray image origination points in space by movement of said C-arm with said single x-ray source and said single x-ray detector mounted thereon;
   with an optical system comprising at least two optical image acquisition units, a first of said optical image acquisition units being mounted for co-movement with said single x-ray source, and a second of said optical image acquisition units being mounted at said support unit, acquiring at least two optical exposures of the examination subject respectively from at least two optical exposure origination points that respectively optically correspond to said at least two different x-ray image origination points; and automatically superimposing the optical exposures with the x-ray images by superimposing the respective optical exposure, from among said at least two optical exposures, with the respective x-ray image, from among said at least two x-ray images that has an x-ray image origination point corresponding to the optical exposure origination point of that optical exposure.

10. An imaging method as claimed in claim 9 comprising acquiring each of said at least two optical exposures as a video sequence.

11. An imaging method as claimed in claim 9 comprising acquiring said at least two optical exposures simultaneously.

12. An imaging method comprising:

using a C-arm imaging system comprising a C-arm that is movable to acquire at least two x-ray images of an examination subject respectively by irradiating the examination subject with x-rays directed at the subject from at least two x-ray image origination points in space;

acquiring at least two optical exposures of the examination subject respectively from at least two optical exposure origination points that respectively optically correspond to said at least two different x-ray image origination points respectively with at least two optical image acquisition units, each having at least two mirrors associated therewith, and positioning said at least two optical image acquisition units and the at least two mirrors associated therewith to direct light from the examination subject via the at least two mirrors to the associated optical image acquisition unit to respectively acquire said at least two optical exposures at said optical exposure origination points respectively corresponding to said at least two x-ray image origination points; and automatically superimposing the optical exposures with the x-ray images by superimposing the respective optical exposure, from among said at least two optical exposures, with the respective x-ray image, from among said at least two x-ray images that has an x-ray image origination point corresponding to the optical exposure origination point of that optical exposure.

13. An imaging method as claimed in claim 12 comprising acquiring said x-ray images using a single movable x-ray source and a single movable x-ray detection unit both mounted on said C-arm.

14. An imaging method as claimed in claim 13 comprising mounting said at least two optical image acquisition units respectively at different positions on said C-arm.

15. An imaging method as claimed in claim 13 comprising mounting a first of said at least two optical image acquisition units for co-movement with said x-ray source, and mounting a second of said at least two optical image acquisition units at said support unit.

16. An imaging method as claimed in claim 12 employing a video camera as each of said optical image acquisition units.

* * * * *